(12) United States Patent
Shen et al.

(10) Patent No.: US 10,982,238 B2
(45) Date of Patent: Apr. 20, 2021

(54) ESCHERICHIA COLI TRANSFORMANT FOR PRODUCING ITACONATE AND USES THEREOF

(71) Applicants: National Tsing Hua University, Hsinchu (TW); Chang Chun Plastics Co., Ltd., Taipei (TW); Chang Chun Petrochemical Co., Ltd., Taipei (TW); DAIREN CHEMICAL CORPORATION, Taipei (TW)

(72) Inventors: Roa-Pu Shen, Hsinchu (TW); Wei Lu, Hsinchu (TW); Tung-Yu Wang, Hsinchu (TW)

(73) Assignees: NATIONAL TSING HUA UNIVERSITY, Hsinchu (TW); CHANG CHUN PLASTICS CO., LTD., Taipei (TW); CHANG CHUN PETROCHEMICAL CO., LTD., Taipei (TW); DAIREN CHEMICAL CORPORATION, Taipei (TW)

(*) Notice: Subject to any disclaimer, the term of this patent is extended or adjusted under 35 U.S.C. 154(b) by 0 days.

(21) Appl. No.: 16/516,464

(22) Filed: Jul. 19, 2019

(65) Prior Publication Data
US 2020/0325503 A1 Oct. 15, 2020

(30) Foreign Application Priority Data
Apr. 11, 2019 (TW) ................. 108112739

(51) Int. Cl.
*C12P 7/44* (2006.01)
*C12N 15/70* (2006.01)
*C12N 1/20* (2006.01)
*C12N 9/02* (2006.01)

(52) U.S. Cl.
CPC .......... *C12P 7/44* (2013.01); *C12N 1/20* (2013.01); *C12N 9/0008* (2013.01); *C12N 15/70* (2013.01); *C12Y 101/01175* (2013.01); *C12Y 203/03001* (2013.01); *C12Y 301/01068* (2013.01); *C12Y 402/01003* (2013.01); *C12Y 402/01082* (2013.01); *C12Y 604/01001* (2013.01)

(58) Field of Classification Search
None
See application file for complete search history.

(56) References Cited

U.S. PATENT DOCUMENTS

2017/0137855 A1* 5/2017 Zhang .................. C12N 9/0006

OTHER PUBLICATIONS

Cao et al. PLoS One. Jul. 5, 2013;8(7):e67305, pp. 1-7 (Year: 2013).*
Tai et al. Nat Chem Biol. Apr. 2016;12(4):247-53. (Year: 2016).*
Chica et al. Curr Opin Biotechnol. Aug. 2005;16(4):378-84. (Year: 2005).*
Singh et al. Curr Protein PeptSci. 2017, 18, 1-11 (Year: 2017).*
Kizer et al. Appl Environ Microbiol. May 2008;74(10):3229-41. (Year: 2008).*
Prather et al. CurrOpin Biotechnol. Oct. 2008;19(5):468-74. (Year: 2008).*
Vuoristo et al. AMB Expr (2015) 5:61 (Year: 2015).*
Chang et al. J Biotechnol. May 10, 2017;249:73-81. Epub Mar. 31, 2017. (Year: 2017).*
Gibson et al. Nat Methods. May 2009;6(5):343-5. Epub Apr. 12, 2009. (Year: 2009).*

* cited by examiner

*Primary Examiner* — Christian L Fronda
(74) *Attorney, Agent, or Firm* — WPAT, PC

(57) ABSTRACT

The present disclosure provides an *Escherichia coli* transformant and a method for producing itaconate using the *Escherichia coli* transformant.

2 Claims, 15 Drawing Sheets
Specification includes a Sequence Listing.

SEQUENCE LISTING

```
<160> NUMBER OF SEQ ID NOS: 30

<210> SEQ ID NO 1
<211> LENGTH: 60
<212> TYPE: DNA
<213> ORGANISM: Artificial Sequence
<220> FEATURE:
<223> OTHER INFORMATION: synthetic primer

<400> SEQUENCE: 1
acgcactgac cgaattcatt aaagaggaga aaggtaccat gtttgaaagg gatatcgtgg     60

<210> SEQ ID NO 2
<211> LENGTH: 60
<212> TYPE: DNA
<213> ORGANISM: Artificial Sequence
<220> FEATURE:
<223> OTHER INFORMATION: synthetic primer

<400> SEQUENCE: 2
ccttaagctt atcgataccg tcgacttagc gctcctcgcg aggaaccaac ttgcgggatt     60

<210> SEQ ID NO 3
<211> LENGTH: 60
<212> TYPE: DNA
<213> ORGANISM: Artificial Sequence
<220> FEATURE:
<223> OTHER INFORMATION: synthetic primer

<400> SEQUENCE: 3
cgctaagtcg acggtatcga taagcttaag gagatatacc atgtcgactc acacatcttc     60

<210> SEQ ID NO 4
<211> LENGTH: 60
```

```
<212> TYPE: DNA
<213> ORGANISM: Artificial Sequence
<220> FEATURE:
<223> OTHER INFORMATION: synthetic primer

<400> SEQUENCE: 4
actgagcctt tcgttttatt tgatgcctct agcacgcgcc ttaggaaacg acgacgatca    60

<210> SEQ ID NO 5
<211> LENGTH: 60
<212> TYPE: DNA
<213> ORGANISM: Artificial Sequence
<220> FEATURE:
<223> OTHER INFORMATION: synthetic primer

<400> SEQUENCE: 5
caccatgact aagcagtcgg cggacagtaa tgcgaagagc ggtgtgacct ctgagatctg    60

<210> SEQ ID NO 6
<211> LENGTH: 60
<212> TYPE: DNA
<213> ORGANISM: Artificial Sequence
<220> FEATURE:
<223> OTHER INFORMATION: synthetic primer

<400> SEQUENCE: 6
ttgatgcctc tagcacgcgt accatgggat cccccgggtt aaaccagtgg ggatttaacc    60

<210> SEQ ID NO 7
<211> LENGTH: 60
<212> TYPE: DNA
<213> ORGANISM: Artificial Sequence
<220> FEATURE:
<223> OTHER INFORMATION: synthetic primer

<400> SEQUENCE: 7
gtttaagtcg acggtatcga taagcttaag gagatatacc atgtcgtcaa ccctacgaga    60

<210> SEQ ID NO 8
<211> LENGTH: 60
<212> TYPE: DNA
<213> ORGANISM: Artificial Sequence
<220> FEATURE:
<223> OTHER INFORMATION: synthetic primer

<400> SEQUENCE: 8
atgcctctag cacgcgtacc atgggatccc ccgggttact tcaacatatt acgaatgaca    60

<210> SEQ ID NO 9
<211> LENGTH: 60
<212> TYPE: DNA
<213> ORGANISM: Artificial Sequence
<220> FEATURE:
<223> OTHER INFORMATION: synthetic primer

<400> SEQUENCE: 9
ttgtccggtt aaatccccac tggtttaaag gagatatacc atggctgata caaaagcaaa    60

<210> SEQ ID NO 10
<211> LENGTH: 60
<212> TYPE: DNA
<213> ORGANISM: Artificial Sequence
<220> FEATURE:
<223> OTHER INFORMATION: synthetic primer

<400> SEQUENCE: 10
```
cacgcgtacc atgggatccc ccgggttagc gctcctcgcg aggaaccaac ttgcgggatt    60

<210> SEQ ID NO 11
<211> LENGTH: 60
<212> TYPE: DNA
<213> ORGANISM: Artificial Sequence
<220> FEATURE:
<223> OTHER INFORMATION: synthetic primer

<400> SEQUENCE: 11
gggtgagttt tgcttttgta tcagccatgg tatatctcct ttaaaccagt ggggatttaa    60

<210> SEQ ID NO 12
<211> LENGTH: 60
<212> TYPE: DNA
<213> ORGANISM: Artificial Sequence
<220> FEATURE:
<223> OTHER INFORMATION: synthetic primer

<400> SEQUENCE: 12
atttgatgcc tctagcacgc gtaccatggg atcccccggg tcattctccg taccaccgg    60

<210> SEQ ID NO 13
<211> LENGTH: 60
<212> TYPE: DNA
<213> ORGANISM: Artificial Sequence
<220> FEATURE:
<223> OTHER INFORMATION: synthetic primer

<400> SEQUENCE: 13
caccatgact aagcagtcgg cggacagtaa tgcgaagagc ggtgtgacct ctgagatctg    60

<210> SEQ ID NO 14
<211> LENGTH: 60
<212> TYPE: DNA
<213> ORGANISM: Artificial Sequence
<220> FEATURE:
<223> OTHER INFORMATION: synthetic primer

<400> SEQUENCE: 14
atttgatgcc tctagcacgc gtaccatggg atcccccggg ttaggaaacg acgacgatca    60

<210> SEQ ID NO 15
<211> LENGTH: 60
<212> TYPE: DNA
<213> ORGANISM: Artificial Sequence
<220> FEATURE:
<223> OTHER INFORMATION: synthetic primer

<400> SEQUENCE: 15
ggacgcactg accgaattca ttaaagagga gaaaggtacc atgagccagt ttgcgaacta    60

<210> SEQ ID NO 16
<211> LENGTH: 60
<212> TYPE: DNA
<213> ORGANISM: Artificial Sequence
<220> FEATURE:
<223> OTHER INFORMATION: synthetic primer

<400> SEQUENCE: 16
atttgatgcc tctagcacgc gtaccatggg atcccccggg tcaaaccgcg cccggactca    60

<210> SEQ ID NO 17
<211> LENGTH: 60
<212> TYPE: DNA
<213> ORGANISM: Artificial Sequence

```
<220> FEATURE:
<223> OTHER INFORMATION: synthetic primer

<400> SEQUENCE: 17
ggacgcactg accgaattca ttaaagagga gaaaggtacc atgtcgtacg caatctatcc    60

<210> SEQ ID NO 18
<211> LENGTH: 60
<212> TYPE: DNA
<213> ORGANISM: Artificial Sequence
<220> FEATURE:
<223> OTHER INFORMATION: synthetic primer

<400> SEQUENCE: 18
tcagccggcg cggtgtggat gctgacatgg tatatctcct ttattgcgcg aagccccatt    60

<210> SEQ ID NO 19
<211> LENGTH: 60
<212> TYPE: DNA
<213> ORGANISM: Artificial Sequence
<220> FEATURE:
<223> OTHER INFORMATION: synthetic primer

<400> SEQUENCE: 19
ccggtgtaaa tggggcttcg cgcaataaag gagatatacc atgtcagcat ccacaccgcg    60

<210> SEQ ID NO 20
<211> LENGTH: 60
<212> TYPE: DNA
<213> ORGANISM: Artificial Sequence
<220> FEATURE:
<223> OTHER INFORMATION: synthetic primer

<400> SEQUENCE: 20
ggaaactgga tgagaagtt gcggacatgg tatatctcct tcagtgcgaa tgcctcggat    60

<210> SEQ ID NO 21
<211> LENGTH: 60
<212> TYPE: DNA
<213> ORGANISM: Artificial Sequence
<220> FEATURE:
<223> OTHER INFORMATION: synthetic primer

<400> SEQUENCE: 21
gcgcggcaat ccgaggcatt cgcactgaag gagatatacc atgtccgcaa cttctccatc    60

<210> SEQ ID NO 22
<211> LENGTH: 60
<212> TYPE: DNA
<213> ORGANISM: Artificial Sequence
<220> FEATURE:
<223> OTHER INFORMATION: synthetic primer

<400> SEQUENCE: 22
actgagcctt tcgttttatt tgatgcctct agcacgcgcc tcaggccgac gcaagcagcc    60

<210> SEQ ID NO 23
<211> LENGTH: 60
<212> TYPE: DNA
<213> ORGANISM: Artificial Sequence
<220> FEATURE:
<223> OTHER INFORMATION: synthetic primer

<400> SEQUENCE: 23
gtttaagtcg acggtatcga taagcttaag gagatatacc atgagccagt tgcgaacta    60
```

<210> SEQ ID NO 24
<211> LENGTH: 60
<212> TYPE: DNA
<213> ORGANISM: Artificial Sequence
<220> FEATURE:
<223> OTHER INFORMATION: synthetic primer

<400> SEQUENCE: 24
agaggctggg atagattgcg tacgacatgg tatatctcct tcaaaccgcg cccggactca    60

<210> SEQ ID NO 25
<211> LENGTH: 60
<212> TYPE: DNA
<213> ORGANISM: Artificial Sequence
<220> FEATURE:
<223> OTHER INFORMATION: synthetic primer

<400> SEQUENCE: 25
ggcgtacgtg agtccgggcg cggtttgaag gagatatacc atgtcgtacg caatctatcc    60

<210> SEQ ID NO 26
<211> LENGTH: 60
<212> TYPE: DNA
<213> ORGANISM: Artificial Sequence
<220> FEATURE:
<223> OTHER INFORMATION: synthetic primer

<400> SEQUENCE: 26
atttgatgcc tctagcacgc gtaccatggg atcccccggg tcattctccg taccacccgg    60

<210> SEQ ID NO 27
<211> LENGTH: 60
<212> TYPE: DNA
<213> ORGANISM: Artificial Sequence
<220> FEATURE:
<223> OTHER INFORMATION: synthetic primer

<400> SEQUENCE: 27
ggacgcactg accgaattca ttaaagagga gaaaggtacc atggctgata caaaagcaaa    60

<210> SEQ ID NO 28
<211> LENGTH: 60
<212> TYPE: DNA
<213> ORGANISM: Artificial Sequence
<220> FEATURE:
<223> OTHER INFORMATION: synthetic primer

<400> SEQUENCE: 28
tggcgacttg atcgtcgtcg tttcctaaag gagatatacc atgaaaattc atcccctgt    60

<210> SEQ ID NO 29
<211> LENGTH: 60
<212> TYPE: DNA
<213> ORGANISM: Artificial Sequence
<220> FEATURE:
<223> OTHER INFORMATION: synthetic primer

<400> SEQUENCE: 29
atacgcagac aggggatga attttcatgg tatatctcct ttaggaaacg acgacgatca    60

<210> SEQ ID NO 30
<211> LENGTH: 20
<212> TYPE: DNA
<213> ORGANISM: Artificial Sequence
<220> FEATURE:
<223> OTHER INFORMATION: synthetic primer

```
<400> SEQUENCE: 30
ggtacctttc tcctctttaa                                                  20
```

ESCHERICHIA COLI TRANSFORMANT FOR PRODUCING ITACONATE AND USES THEREOF

CROSS-REFERENCE TO RELATED APPLICATION

This application claims priority of Taiwan patent application No. 108112739, filed on Apr. 11, 2019, the content of which is incorporated herein in its entirety by reference.

BACKGROUND OF THE INVENTION

1. Field of the Invention

The present invention relates to an *Escherichia coli* transformant and a method for producing itaconate using the *Escherichia coli* transformant.

2. The Prior Art

Recently, recycled materials obtained by converting biomass have received more and more attention. Itaconate (IA) is a C5 dicarboxylic acid with bifunctional groups and an unsaturated double bond, making it useful in the field of polymer synthesis. Itaconate has once been proposed by the US Department of Energy (DOE) to be the top 12 value added bio-based chemicals. Moreover, IA plays a significant role in sustainability for being a renewable substitute of a variety of petroleum-based chemical such as acrylic acid and methacrylic acid, so as to reduce the reliance on oil-based resources and long-term environment damages. IA has the following chemical structure:

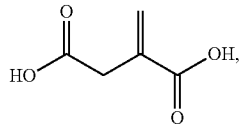

and is an essential precursor for many products (e.g., polypropylene fibers, rubber, artificial diamonds, and lenses), which are widely used in the chemical industry. Traditionally, IA has been isolated from *Aspergillus terreus*. However, the growth of *Aspergillus terreus* is slow and *Aspergillus terreus* cannot produce IA during the sporulation period. Therefore, there is a need in the industry for a method for mass production of IA.

*Escherichia coli* (usually abbreviated: *E. coli*) is a bacterium in the gut of humans and animals, mainly parasitic in the large intestine, accounting for about 0.1% of intestinal bacteria. *Escherichia coli* is a Gram-negative, facultative anaerobic, rod-shaped, coliform bacterium of the genus *Escherichia*.

Although researchers in the field have found that *E. coli* can be used to produce IA. However, in the *E. coli* strains, in order to accumulate the precursors for producing IA, it is necessary to inhibit the important gene icd which encodes isocitrate dehydrogenase in the citric acid cycle, and inhibiting the icd gene causes α-ketoglutaric acid (α-KG) and glutamate auxotrophs, making the strains unable to grow and produce IA in basal medium. In view of this long-standing problem, the conventional technique is to provide the essential amino acid (i.e., glutamate) which cannot be synthesized by the IA producing strain inhibiting the icd gene by additionally adding protein nutrients (for example, yeast extract or glutamate) to help the strain grow.

However, the addition of protein nutrients to the IA producing strain results in an increase in overall production costs. Therefore, if *Escherichia coli* that can produce IA without additional protein nutrients can be developed, there is opportunity to reduce the production cost of IA, and it will benefit a large group of people in need thereof and bring about considerable breakthroughs in the technology of the field.

SUMMARY OF THE INVENTION

A primary objective of the present invention is to provide an *Escherichia coli* transformant, comprising at least one plasmid, wherein the at least one plasmid includes a D-xylose dehydrogenase (XDH) gene, a D-xylonolactonase (XL) gene, a 2-keto-3-deoxy-D-xylonate dehydratase (KdxD) gene, and a 2-ketoglutarate semialdehyde dehydrogenase (KGSADH) gene; wherein an isocitrate dehydrogenase (icd) gene of the *Escherichia coli* transformant is deleted.

According to an embodiment of the present invention, the at least one plasmid further includes a D-xylonate dehydratase (XD) gene.

According to an embodiment of the present invention, the XDH gene, the XL gene, the KdxD gene, the KGSADH gene, and the XD gene are obtained from *Burkholderia xenovorans* strains.

According to an embodiment of the present invention, the XDH gene, the XL gene, the XD gene, the KdxD gene, and the KGSADH gene are sequentially constructed from their 5' ends to 3' ends in the at least one plasmid.

According to an embodiment of the present invention, the *Escherichia coli* transformant is a transformant of *Escherichia coli* BW25113 or a transformant of *Escherichia coli* XL-1 Blue.

According to an embodiment of the present invention, the *Escherichia coli* transformant converts xylose into α-ketoglutaric acid through a nonphosphorylative metabolic pathway.

According to an embodiment of the present invention, a xylose isomerase gene (xylA), a 2-dehydro-3-deoxy-D-pentonate aldolase gene (yjhH), and a 2-keto-3-deoxygluconate aldolase gene (yagE) of the *Escherichia coli* transformant are deleted.

According to an embodiment of the present invention, the *Escherichia coli* transformant further comprises a citrate synthase (gltA), an aconitase B (acn B), and a pyruvate carboxylase (pyc).

According to an embodiment of the present invention, the *Escherichia coli* transformant produces itaconate (IA).

According to an embodiment of the present invention, the *Escherichia coli* transformant produces itaconate without adding a yeast extract or glutamate.

Another objective of the present invention is to provide a method for producing itaconate using the above mentioned *Escherichia coli* transformant, comprising the following steps: (a) transforming the at least one plasmid into cells of *Escherichia coli* to obtain the *Escherichia coli* transformant; (b) providing a substrate as a culture environment, wherein the substrate comprises a carbon source, a nitrogen source, minerals, and vitamins; and (c) cultivating the *Escherichia coli* transformant at a temperature ranging from 30° C. to 37° C. and a dissolved oxygen ranging from 20% to 30%, and inducing the *Escherichia coli* transformant to produce itaconate.

According to an embodiment of the present invention, the carbon source in step (b) comprises a glycerol, and the nitrogen source is an ammonium salt.

According to an embodiment of the present invention, the carbon source in step (b) further comprises a xylose, and an initial concentration of the xylose is ranging from 2 g/L to 10 g/L.

According to an embodiment of the present invention, the *Escherichia coli* transformant produces 1.2 g/L to 2.2 g/L itaconate every 24 hours.

According to an embodiment of the present invention, the *Escherichia coli* transformant produces 19 g/L to 21 g/L itaconate every 90 hours.

According to an embodiment of the present invention, the *Escherichia coli* transformant produces itaconate without adding a yeast extract or glutamate.

In summary, the *Escherichia coli* transformant of the present invention has the effect of: by constructing a heterologous metabolic pathway, the nonphosphorylative pathway of *Burkholderia xenovorans* in *Escherichia coli*, enables the strain to self-convert to synthesize α-ketoglutaric acid and further synthesize glutamate by metabolizing xylose. Furthermore, in the medium without additional protein nutrient source, the growth of the *Escherichia coli* transformant of the present invention is optimized that the original cell concentration of $OD_{600}$ is 0.296 (36 hours) (before optimization of gene combination), and the optimized cell concentration of $OD_{600}$ is 1.62 (36 hours)(after optimization of gene combination) through the optimization of gene combination. Using glycerol and xylose can increase IA production and optimize cell growth, and the yield of IA can reach 1.2 g/L (24 hours) by eliminating the competitive pathways of the nonphosphorylative metabolic pathway. The experimental results of the present invention confirm that reducing the initial concentration of xylose in the medium can increase the yield of IA by 2.2 g/L (24 hours), and in combination with the above optimized conditions, the process is amplified in a 1 liter fermentation tank (i.e., a bioreactor), the yield of IA can achieve 20.01 g/L (90 hours), 0.62 (g IA/g glycerol), and 0.24 g/L/hour productivity in minimal medium.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
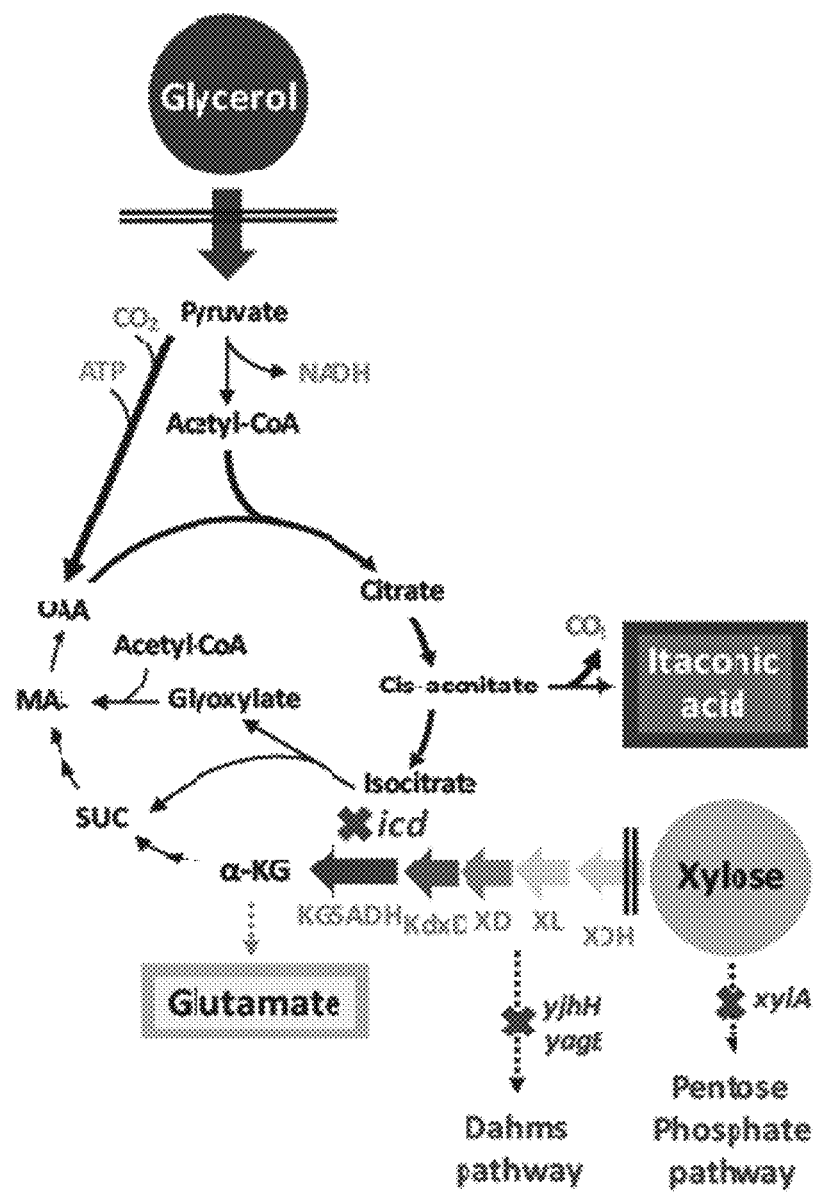
FIG. 1 is a schematic diagram showing the pathway to decouple IA production from endogenous α-ketoglutaric acid biosynthesis in the *Escherichia coli* transformant of the present invention, in which α-KG represents α-ketoglutaric acid; OAA represents oxaloacetate; MAL represents malate; SUC represents succinate; acnB represents aconitase B; cad represents cis-aconitate decarboxylase; pyc represents pyruvate carboxylase; gltA represents citrate synthase; icd represents gene encoding isocitrate dehydrogenase; xylA represents gene encoding xylose isomerase; yjhH represents gene encoding 2-dehydro-3-deoxy-D-pentonate aldolase; yagE represents gene encoding 2-keto-3-deoxygluconate aldolase; XDH represents gene encoding D-xylose dehydrogenase; XL represents gene encoding D-xylonolactonase; XD represents gene encoding D-xylonate dehydratase; KdxD represents gene encoding 2-keto-3-deoxy-D-xylonate dehydratase; KGSADH represents gene encoding 2-ketoglutarate semialdehyde dehydrogenase.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the terms "expression plasmid" and "expression vector" can be used interchangeably, and refer to any recombinant expression system that can constitutively or inducibly express a selected nucleic acid sequence in any competent host cell in vitro or in vivo. The expression plasmid can be a linear or circular expression system and encompasses an expression system that maintains the episomal form or is integrated into the genome of the host cell. The recombinant expression system may or may not have the ability to self-replicate, and it may only drive the transient expression of the host cell.

According to the present invention, α-ketoglutaric acid is the end product of nonphosphorylative pathways, and is essential for *E. coli* to grow. Inactivation of icd turns *E. coli* into both α-ketoglutarate and glutamate auxotroph. Rescuing α-ketoglutarate auxotroph via nonphosphorylative pathways serves as a selection force to discover new functional gene clusters.

Example 1

Pathway to Decouple Itaconate Production from Endogenous α-Ketoglutaric Acid Biosynthesis in *Escherichia coli* Transformant of Present Invention In this example and the following examples, all chemicals and reagents were purchased from Sigma-Aldrich (Saint Louis, Mo.) unless otherwise specified. KOD DNA polymerase and KOD Xtreme DNA polymerase were purchased from EMD Chemicals (San Diego, Calif.). All oligonucleotides were synthesized from IDT (Singapore).

All strains, plasmids and their genotypes are shown in Table 1 and Table 2. All gene fragments were amplified by corresponding primers listed in Table 3. The reference of the D-xylose dehydrogenase (XDH) gene, the D-xylonolactonase (XL) gene, the 2-keto-3-deoxy-D-xylonate dehydratase (KdxD) gene, and the 2-ketoglutarate semialdehyde dehydrogenase (KGSADH) gene from *Escherichia coli* is Tai, Y. et al., *Engineering Nonphosphorylative Metabolism to Generate Lignocellulose-derived Products*. Nature, 2016. The reference of the isocitrate dehydrogenase (icd) gene from *Escherichia coli* is Chang, P., et al., *Engineering efficient production of itaconic acid from diverse substrates in Escherichia coli*. J Biotechnol, 2017. All plasmids were constructed by Gibson DNA assembly with purified fragments (see Gibson, D. G, et al., *Enzymatic assembly of DNA molecules up to several hundred kilobases*. Nat Methods, 2009. 6(5): p. 343-5). All plasmids were then propagated in XL-1 Blue (Stratagene). Host gene deletion of icd, xylA, yagE, yjhH, maeA and maeB was achieved by P1 transduction using the Keio collection strains as the donor (see Baba, T., et al., *Construction of Escherichia coli K-12 in-frame, single-gene knockout mutants: the Keio collection*. Mol Syst Biol, 2006. 2: p. 2006 0008). The $kan^R$ insertion into the target gene region was further removed as described in Datsenko, K. A. and B. L. Wanner, *One-step inactivation of chromosomal genes in Escherichia coli K-12 using PCR products*. Proc Natl Acad Sci USA, 2000. 97(12): p. 6640-5.

TABLE 1

| Strain | Genotype | Reference |
|---|---|---|
| *E. coli* strain BW25113 | rrnB$_{T14}$ ΔlacZ$_{WJ16}$hsdR514 ΔaraBAD$_{AH33}$ ΔrhaBAD$_{LD78}$ | Datsenko, K. A. and B. L. Wanner, One-step inactivation of chromosomal genes in *Escherichia coli* K-12 using PCR products. Proc. Natl. Acad. Sci. U.S.A., 2000. 97(12): p. 6640-5 |
| *E. coli* strain XL-1 Blue | recA1 endA1 gyrA96 thi-1 hsdR17 supE44 relA1 lac [F' proAB lacI$^q$ZΔM15 Tn10 (Tet$^R$)] | Stratagene |

TABLE 1-continued

| Strain | Genotype | Reference |
|---|---|---|
| E. coli strain BW25113 Δicd | BW25113 Δicd | Chang, P., et al., Engineering efficient production of itaconic acid from diverse substrates in Escherichia coli. J Biotechnol, 2017. 249: p. 73-81 |
| E. coli strain BW25113 ΔxylAΔyjhHΔyagEΔicd | BW25113 ΔxylAΔyjhHΔyagEΔicd | Present invention |
| E. coli strain BW25113 ΔxylAΔyjhHΔyagEΔicd ΔmaeAΔmaeB | BW25113 ΔxylAΔyjhHΔyagEΔicdΔmaeA ΔmaeB | Present invention |

TABLE 2

| Plasmid | Genotype | Reference |
|---|---|---|
| PGC07 | P15A origin, SpecR, PLlacO1: gltA(EC)pyc(CG) | Chang, P, et al., Engineering efficient production of itaconic acid from diverse substrates in Escherichia coli. J Biotechnol, 2017. 249: p. 73-81 |
| pPC150 | ColE1 origin, KanR, PLlacO1: cad(AT) | Chang, P, et al., Engineering efficient production of itaconic acid from diverse substrates in Escherichia coli. J Biotechnol, 2017. 249: p. 73-81 |
| pPC168 | ColE1 origin, KanR, PLlacO1: cad(AT)acnB(EC) | Chang, P, et al., Engineering efficient production of itaconic acid from diverse substrates in Escherichia coli. J Biotechnol, 2017. 249: p. 73-81 |
| pKL01 | P15A origin, SpecR, PLlacO1: gltA(CG)pyc(CG) | Present invention |
| pKL02 | ColE1 origin, KanR, PLlacO1: cad(AT)acnA(EC) | Present invention |
| pKL03 | ColE1 origin, KanR, PLlacO1: cad(AT)gltA(EC) | Present invention |
| pKL04 | ColE1 origin, KanR, PLlacO1: cad(AT)gltA(EC) pyc(CG) | Present invention |
| pKL05 | ColE1 origin, AmpR, PLlacO1: KGSADH | Present invention |
| pKL06 | P15A origin, SpecR, PLlacO1: XDH-XL-XD-KdxD | Present invention |
| pKL07 | ColE1 origin, KanR, PLlacO1: cad- KGSADH-XDH | Present invention |
| pKL08 | P15A origin, SpecR, PLlacO1: gltA(EC)pyc(CG)-XL-XD-KdxD | Present invention |

TABLE 3

| Primers | SEQ ID No. | Purpose |
|---|---|---|
| IA28 | 1 | Forward primer of gltA(CG) in pKL01 cloning |
| IA29 | 2 | Reverse primer of gltA(CG) in pKL01 cloning |
| IA30 | 3 | Forward primer of pyc(CG) in pKL01 cloning |
| IA31 | 4 | Reverse primer of pyc(CG) in pKL01/8 cloning |
| IA03 | 5 | Forward primer of cad(AT) in pKL02 cloning |
| IA24 | 6 | Reverse primer of cad(AT) in pKL02 cloning |
| IA26 | 7 | Forward primer of acnA(EC) in pKL02 cloning |
| IA27 | 8 | Reverse primer of acnA(EC) in pKL02 cloning |
| IA05 | 9 | Forward primer of gltA(EC) in pKL03 cloning |
| IA35 | 10 | Reverse primer of gltA(EC) in pKL03 cloning |
| IA04 | 11 | Reverse primer of cad(AT) in pKL03 cloning |
| cad-pLac f | 12 | Forward primer of cad(AT) in pKL03 cloning |
| IA03 | 13 | Forward primer in pKL04 cloning |
| IA06 | 14 | Reverse primer in pKL04 cloning |
| IAX3 | 15 | Forward primer in pKL05 cloning |
| IAX4 | 16 | Reverse primer in pKL05 cloning |
| IAX8 | 17 | Forward primer of XDH-XL cloning |
| IAX9 | 18 | Reverse primer of XDH-XL cloning |
| IAX10 | 19 | Forward primer of XD cloning |
| IAX11 | 20 | Reverse primer of XD cloning |
| IAX12 | 21 | Forward primer of KdxD cloning |
| IAX13 | 22 | Reverse primer of KdxD cloning |
| IA53 | 23 | Forward primer of pKL07 cloning |
| IA54 | 24 | Reverse primer of pKL07 cloning |
| IA55 | 25 | Forward primer of pKL07 cloning |
| IA56 | 26 | Reverse primer of pKL07 cloning |
| IA49 | 27 | Forward primer of pKL08 cloning |
| IA51 | 28 | Forward primer of pKL08 cloning |
| IA50 | 29 | Reverse primer of pKL08 cloning |
| IAX02 | 30 | Reverse primer of pKL08 cloning |

For the itaconate (IA) production under the expression of nonphosphorylative pathway, single colonies were chosen from LB plates and inoculated into 2 mL of LB media contained in test tubes with the appropriate antibiotics (kanamycin 50 μg/mL and spectinomycin 50 μg/mL). The overnight culture grown in LB at 37° C. in a rotary shaker (250 rpm) was then inoculated (1%, v/v) into 20 mL of M9 medium (12.8 g $Na_2HPO_4.7H_2O$, 3 g $KH_2PO_4$, 0.5 g NaCl, 1 g $NH_4Cl$, 1 mmol $MgSO_4$, 1 mg vitamin B1 and 0.1 mmol $CaCl_2$ per liter of water), 1000× trace metal mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 0.049 g Co $(NO_3)_2.6H_2O$ per liter water), 10 g/L glycerol with xylose (2, 5, 10, 20 g/L being test separately) and appropriate antibiotics in 250 mL baffled flask with screwed cap. The cultures were grown at 37° C. in a rotary shaker (250 rpm) to an $OD_{600}$ of 0.3-0.4, then induced with 0.1 mM IPTG The induced cultures were grown at 30° C. in a rotary shaker (250 rpm). Samples were taken throughout the production period, centrifuged for HPLC analysis.

Product samples were applied (0.02 mL) to an Agilent Technologies 1260 infinity HPLC equipped with an auto-sampler (Agilent Technologies) and an Agilent Hi-Plex H column (5 mM $H_2SO_4$, 0.6 mL/min, column temperature at 50° C.). Organic acids were detected using a photodiode array detector at 210 nm or 254 nm. Xylose and glycerol were detected using refractive index (RI Detector). Concentrations were determined by extrapolation from standard curves.

For the itaconate production experiment for optimizing the IA production pathway genes, 5 g/L yeast extract and 20 g/L glucose were added. For the ammonium salts experiment, medium was adjusted pH every 12 hours and fed with 5 g/L xylose and 5 g/L glycerol with different amount of ammonium salts. For the growth curve experiment, using the same culture medium (i.e., M9 medium) and carbon source as itaconate production under the expression of nonphosphorylative pathway experiment. Culture temperature was kept at 37° C.

In this example, to achieve efficient IA production, icd inactivation (or knockout) is a necessary strategy. However, it accompanies with additional supply of nutrients such as yeast extract and glutamate to resolve glutamate auxotrophy. The extra production cost may hinder IA production commercialization. In order to decouple IA production and alpha-ketoglutarate (α-KG) biosynthesis in icd inactivated E. coli, the nonphosphorylative pathway was recruited to convert xylose into α-KG so as to resolve the concern of glutamate auxotrophy. For IA production, genes such as cis-aconitate decarboxylase (CAD) from Aspergillus terreus, citrate synthase (gltA) from E. coli and pyruvate carboxylase (pyc) from Corynebacterium glutamicum (CG) were selectively overexpressed, and isocitrate dehydrogenase (icd) gene was completely blocked via gene deletion for efficient IA production.

For the nonphosphorylative pathway, gene cluster from Burkholderia xenovorans, which was demonstrated to functionally convert xylose into α-KG was included. Xylose isomerase (XylA) gene, 2-keto-3-deoxygluconate aldolase (yagE) gene and 2-dehydro-3-deoxy-D-pentonate aldolase (yjhH) gene were further inactivated to reduce the competition between the endogenous metabolic pathway of E. coli and the target metabolic pathway for intermediate metabolites. Glycerol derived from biodiesel production industry is an abundant byproduct and thus is an attractive candidate for bioconversion carbon source. Moreover, glycerol assimilation pathway will generate more energy (as the form of adenosine triphosphate, ATP) compared to utilization of glucose and xylose. Xylose ranks as the major sugars in lignocellulosic hydrolysate. The schematic diagram showing the pathway to decouple IA production from endogenous α-ketoglutaric acid biosynthesis in the Escherichia coli transformant of the present invention is shown in FIG. 1.

FIG. 1 is a schematic diagram showing the pathway to decouple IA production from endogenous α-ketoglutaric acid biosynthesis in the Escherichia coli transformant of the present invention. As shown in FIG. 1, the E. coli transformant of the present invention (icd gene is inactivated) converts xylose into α-KG through the nonphosphorylative metabolic pathway (expressing the XDH gene, the XL gene, the XD gene, the KdxD gene, and the KGSADH gene), which is different from the traditional pathway of endogenous α-KG biosynthesis, so that IA can be produced without adding additional protein nutrients, such as yeast extract or glutamate.

Example 2

Figure 2:
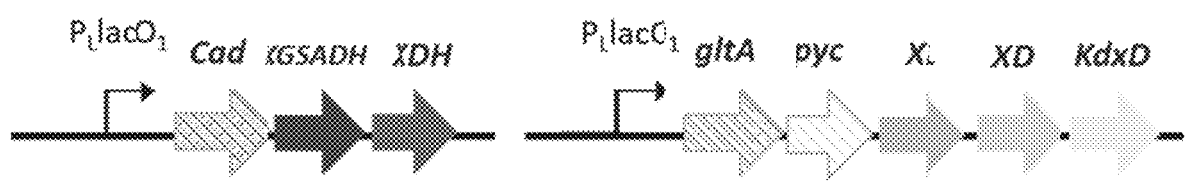
FIG. 2 is a schematic diagram showing the gene combination for constructing a nonphosphorylative pathway using the *Escherichia coli* transformant of the present invention, in which KGSADH represents gene encoding 2-ketoglutarate semialdehyde dehydrogenase (KGSADH); KdxD represents gene encoding 2-keto-3-deoxy-D-xylonate dehydratase (KdxD); XD represents gene encoding D-xylonate dehydratase; XL represents gene encoding D-xylonolactonase (XL); XDH represents gene encoding D-xylose dehydrogenase (XDH); Cad represents gene encoding cis-aconitate decarboxylase; pyc represents gene encoding pyruvate carboxylase; gltA represents gene encoding citrate synthase.

Constructing Nonphosphorylative Pathway Using Escherichia coli Transformant of Present Invention Icd knockout makes the cell lose the ability to convert isocitrate into α-KG and the cell needs extra supply of α-KG FIG. 2 is a schematic diagram showing the gene combination for constructing a nonphosphorylative pathway using the Escherichia coli transformant of the present invention. As shown in FIG. 2, the gene cluster of Burkholderia xenovorans is recruited and the operon structure is further optimized for improving cell growth. In particular, the expression of the XDH gene is expressed by a high-expression plasmid to enhance gene expression in the strain.

Figure 3:
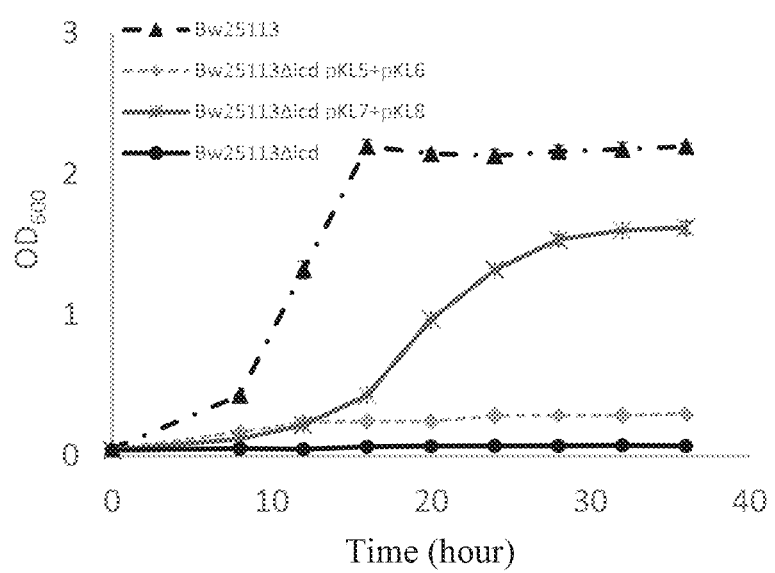
FIG. 3 is a diagram showing growth curves of different operon structures of the *Escherichia coli* transformant of the present invention, in which BW5113 Δicd+pKL5+pKL6 indicates the phenotype of transforming pKL5 and pKL6 plasmids into the *Escherichia coli* strain; BW25113 Δicd+pKL7+pKL8 indicates the phenotype of transforming pKL7 and pKL8 plasmids into the *Escherichia coli* strain.

FIG. 3 is a diagram showing growth curves of different operon structures of the Escherichia coli transformant of the present invention. The results of this example show that using the E. coli transformant of the present invention to construct a nonphosphorylative pathway can enhance cell growth to $OD_{600}$ of up to 1.6 in 36 hours without exogenous supply of α-KG.

Example 3

Determination of IA Production Cultivation Condition Under Expression of IA Pathway and Nonphosphorylative Pathway of Present Invention To improve the metabolic pathway efficiency, it is common to block competing pathways. Therefore, the native xylose isomerase (xylA), 2-dehydro-3-deoxy-D-pentonate aldolase (yjhH) and 2-keto-3-deoxygluconate aldolase (yagE) in E. coli are blocked (the deletion of competitive pathways for non-phosphorylation is shown in FIG. 1), so that the E. coli transformant (BW25113 Δicd ΔxylA ΔyjhH ΔyagE) is constructed for following experiments.

Researchers have suggested that the supply of ammonium salts as nitrogen source which can accumulate more cell mass (see Harder, B. J., K. Bettenbrock, and S Klamt, Temperature-dependent dynamic control of the TCA cycle increases volumetric productivity of itaconic acid production by Escherichia coli. Biotechnol Bioeng, 2018. 115(1): p. 156-164). Therefore, the effect of supply of ammonium salts on IA production is investigated in the present invention. Cell mass is positively correlated with IA production (g/L), and can accumulate more activated transformants, thereby increasing IA production. The results are shown in FIGS. 4A-4D.

Figure 4A:
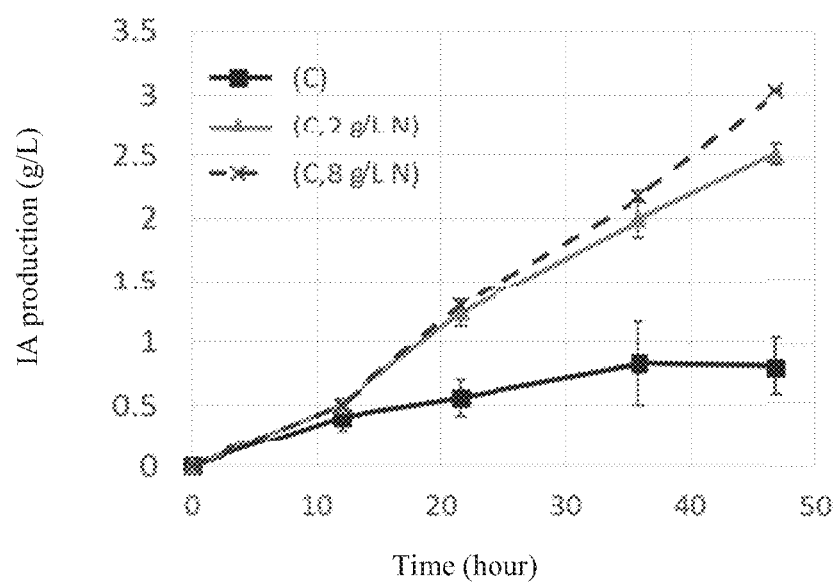
FIG. 4A is a data diagram showing the effect of IA production in the environment fed with ammonium salts (($NH_4)_2SO_4$) by the *Escherichia coli* transformant BW25113 Δicd ΔxylA ΔyjhH ΔyagE of the present invention, in which C represents only fed with 5 g/L glycerol and xylose; C-2 g/L N represents fed with 5 g/L glycerol, xylose and 2 g/L ($NH_4)_2SO_4$; C-8 g/L N represents fed with 5 g/L glycerol, xylose and 8 g/L ($NH_4)_2SO_4$.
Figure 4B:
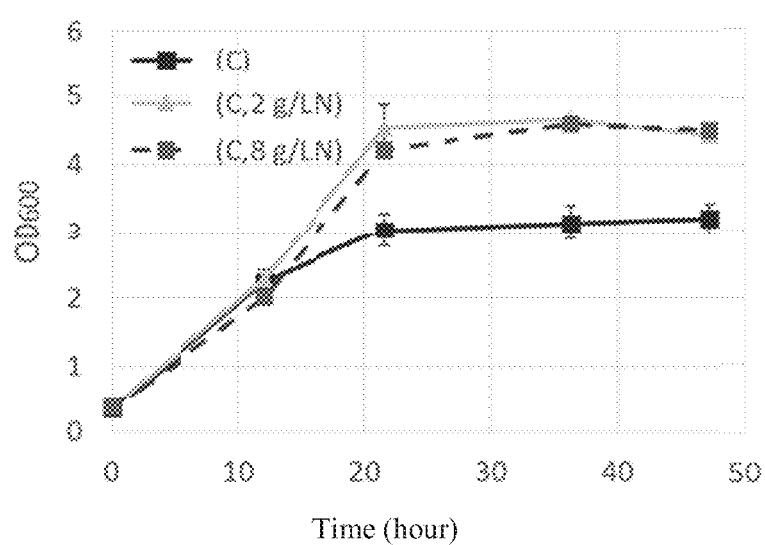
FIG. 4B is a data diagram showing the cell density of the *Escherichia coli* transformant BW25113 Δicd ΔxylA ΔyjhH ΔyagE of the present invention in the environment fed with ammonium salts (($NH_4)_2SO_4$), in which C represents only fed with 5 g/L glycerol and xylose; C-2 g/L N represents fed with 5 g/L glycerol, xylose and 2 g/L ($NH_4)_2SO_4$; C-8 g/L N represents fed with 5 g/L glycerol, xylose and 8 g/L ($NH_4)_2SO_4$.
Figure 4C:
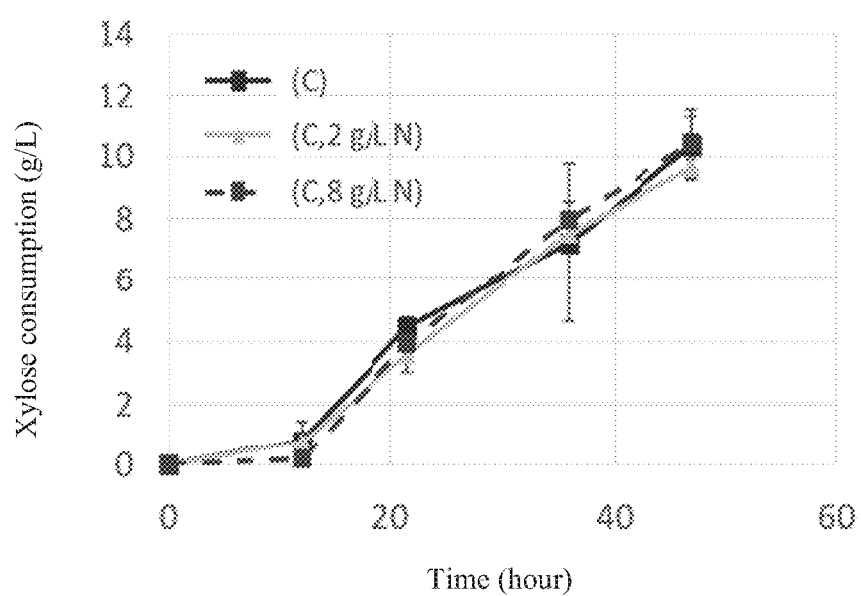
FIG. 4C is a data diagram showing the xylose consumption of the *Escherichia coli* transformant BW25113 Δicd ΔxylA ΔyjhH ΔyagE of the present invention in the environment fed with ammonium salts (($NH_4)_2SO_4$), in which C represents only fed with 5 g/L glycerol and xylose; C-2 g/L N represents fed with 5 g/L glycerol, xylose and 2 g/L ($NH_4)_2SO_4$; C-8 g/L N represents fed with 5 g/L glycerol, xylose and 8 g/L ($NH_4)_2SO_4$.
Figure 4D:
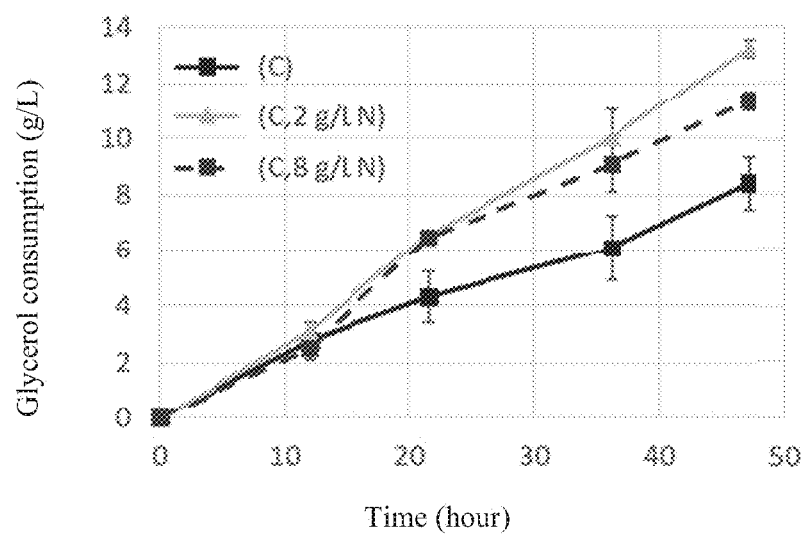
FIG. 4D is a data diagram showing the glycerol consumption of the *Escherichia coli* transformant BW25113 Δicd ΔxylA ΔyjhH ΔyagE of the present invention in the environment fed with ammonium salts (($NH_4)_2SO_4$), in which C represents only fed with 5 g/L glycerol and xylose; C-2 g/L N represents fed with 5 g/L glycerol, xylose and 2 g/L ($NH_4)_2SO_4$; C-8 g/L N represents fed with 5 g/L glycerol, xylose and 8 g/L ($NH_4)_2SO_4$.

FIG. 4A is a data diagram showing the effect of IA production in the environment fed with ammonium salts (($NH_4$)$_2SO_4$) by the Escherichia coli transformant BW25113 Δicd ΔxylA ΔyjhH ΔyagE of the present invention. FIG. 4B is a data diagram showing the cell density of the Escherichia coli transformant BW25113 Δicd ΔxylA ΔyjhH ΔyagE of the present invention in the environment fed with ammonium salts (($NH_4$)$_2SO_4$). FIG. 4C is a data diagram showing the xylose consumption of the Escherichia coli transformant BW25113 Δicd ΔxylA ΔyjhH ΔyagE of the present invention in the environment fed with ammonium salts (($NH_4$)$_2SO_4$). FIG. 4D is a data diagram showing the glycerol consumption of the Escherichia coli transformant BW25113 Δicd ΔxylA ΔyjhH ΔyagE of the present invention in the environment fed with ammonium salts (($NH_4$)$_2SO_4$). As shown in FIGS. 4A and 4B, there is a significant difference between feeding with or without ammonium salt (the "C" group in FIGS. 4A and 4B indicates no supply of ammonium salt, and other groups indicate supply of ammonium salt). Higher cell mass and IA production was achieved by extra supply of ammonium salts. Supplying ammonium salts prolonged IA production as well. However, whether it is 2 g/L ($NH_4$)$_2SO_4$ or 8 g/L ($NH_4$)$_2SO_4$, the feeding amount of nitrogen salts shows no big difference. In addition, the group fed only with glycerol and xylose as carbon source ended up with lower glycerol consumption but almost the same amount of xylose consumption as the group fed with ammonium salts (see FIGS. 4C and 4D), which may cause by the accumulation of α-KG result from limited amount of nitrogen resource. The nitrogen source is a cofactor in the metabolic pathway for converting α-KG into glutamate, so if there is no supply of nitrogen source, it may lead to a decrease in the conversion efficiency of the metabolic pathway, and accumulate α-KG. Hence, glycerol derived carbon flux from central metabolism cannot enter the TCA cycle which result in lower glycerol consumption.

Example 4

Figure 5A:
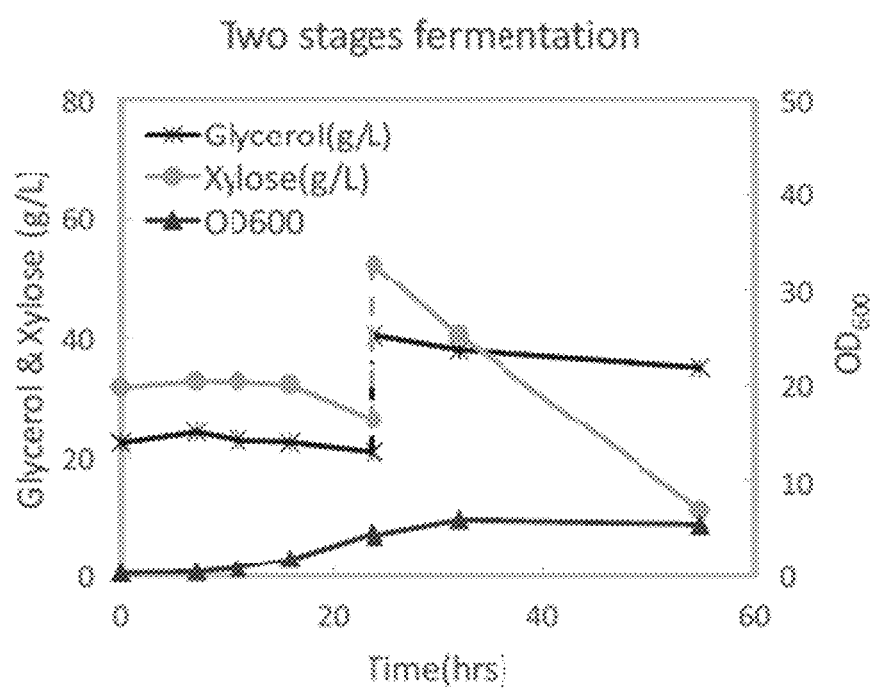
FIG. 5A is a data diagram of glycerol and xylose consumption under two stages fermentation.
Figure 5B:
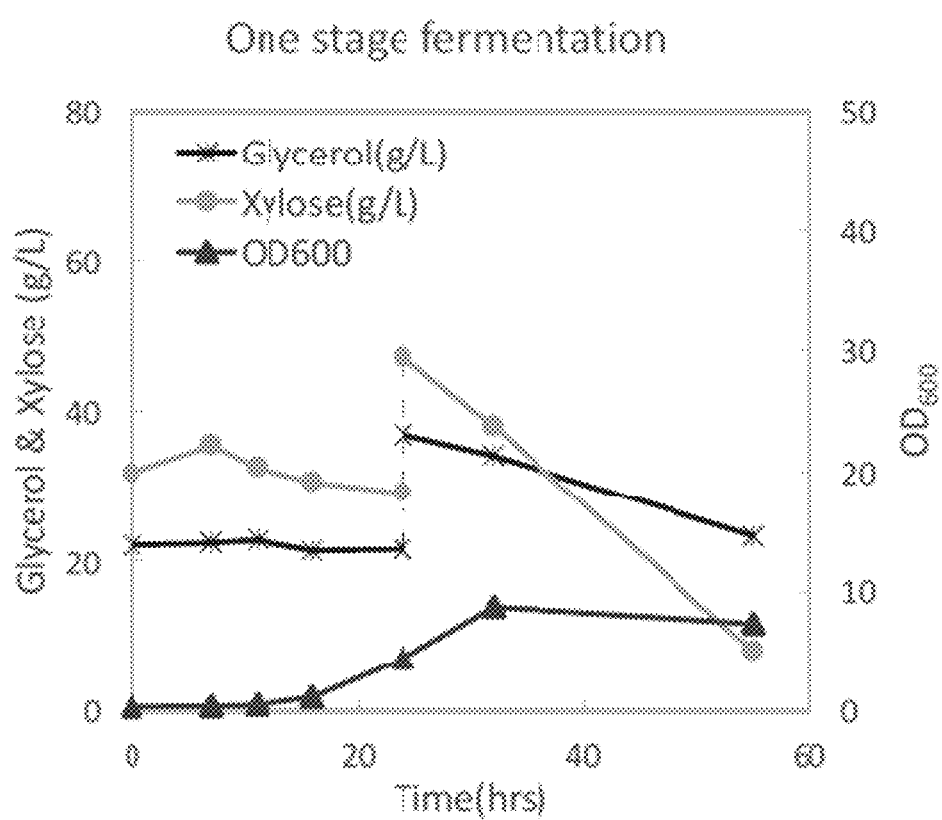
FIG. 5B is a data diagram of glycerol and xylose consumption under one stage fermentation.
Figure 6A:
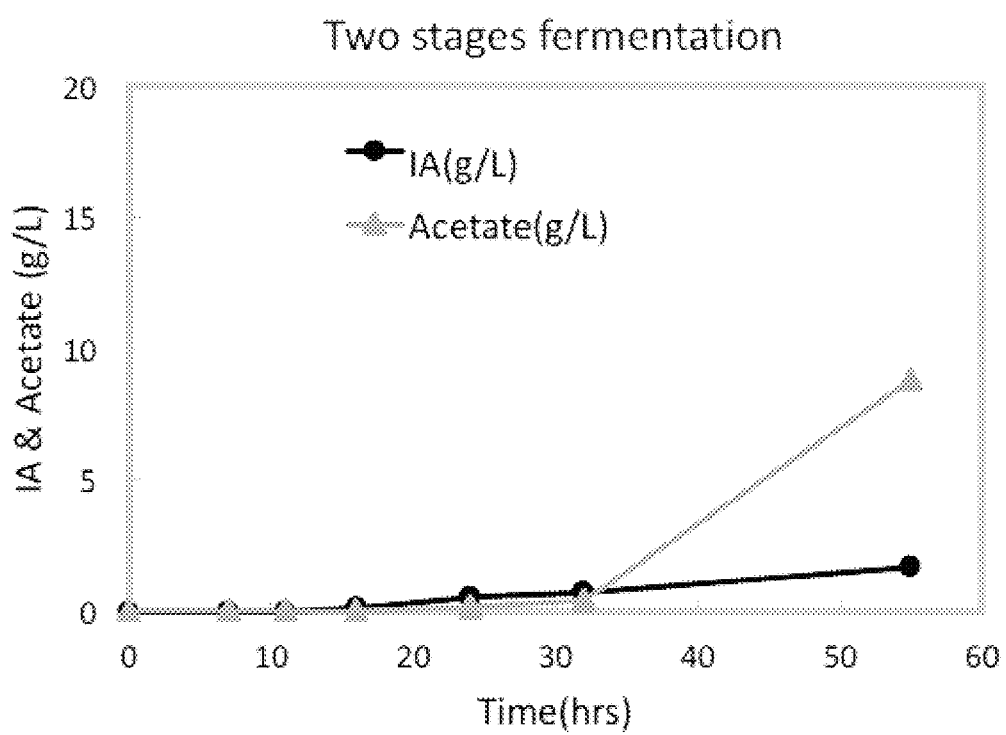
FIG. 6A is a data diagram of IA production titer and acetate titer under two stages fermentation.
Figure 6B:
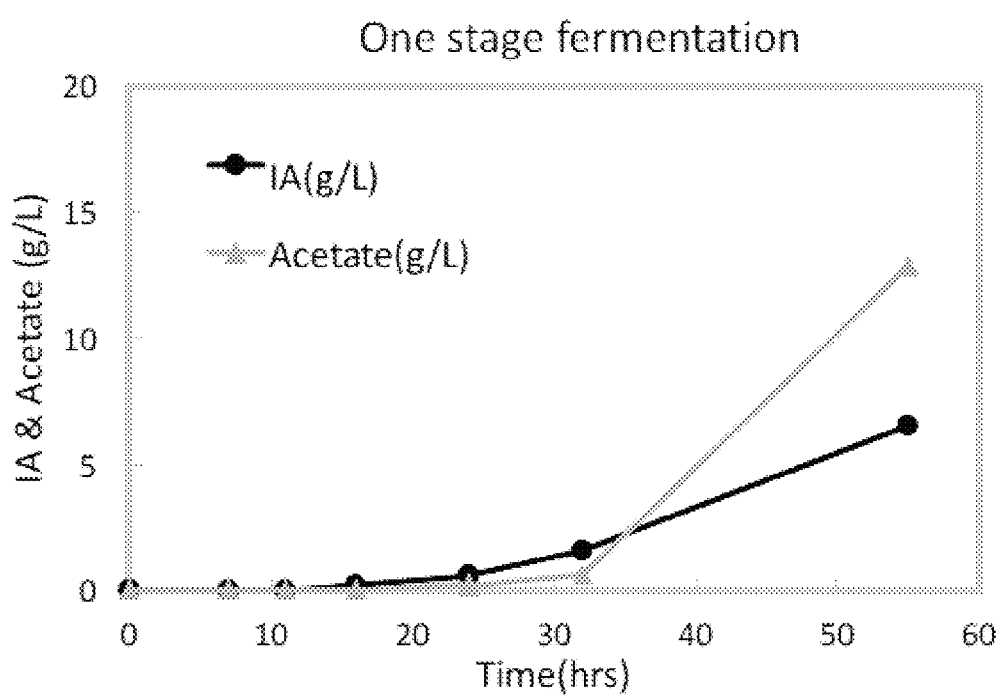
FIG. 6B is a data diagram of IA production titer and acetate titer under one stage fermentation.

Effect Evaluation of IA Production Scaled Up in Bioreactor by *Escherichia coli* Transformant of Present Invention Combined previous examples on designing synergistic operons of IA and nonphosphorylative pathway, optimized IA production via substrate coutilization and extra supply of ammonium salts, the process was attempted to scale up by 1 L bioreactor which can consistently control pH, temperature and dissolved oxygen (DO). Cad protein prefer folding and function under lower temperature in *E. coli* of the present invention. Hence, two different culture temperatures and DO 20% were first tested. First condition, starting temperature was 37° C. and changed to 30° C. when $OD_{600}$ reaches about 0.6 which was called two-stage fermentation. Second condition kept at 30° C. throughout the whole production process which was called one-stage fermentation. The results are shown in FIG. 5A, FIG. 5B, FIG. 6A and FIG. 6B. FIG. 5A is a data diagram of glycerol and xylose consumption under two stages fermentation. FIG. 5B is a data diagram of glycerol and xylose consumption under one stage fermentation. FIG. 6A is a data diagram of IA production titer and acetate titer under two stages fermentation. FIG. 6B is a data diagram of IA production titer and acetate titer under one stage fermentation. As shown in FIG. 5A and FIG. 5B, two-stages process exhibited slightly faster growth in the first 16 hours which probably due to higher cultivation temperature. One-stage fermentation consumed approximately 4-fold glycerol compared to two-stages process which may result from the correct folding of Cad under lower temperature (see FIG. 5A, FIG. 5B, FIG. 6A and FIG. 6B). Glycerol consumption reflected on the IA titer as well. Unexpectedly, lots of xylose were consumed compared to glycerol. Though the significant consumption difference was not shown in the flask experiment, carbon source of the strain of the present invention prefers sugar such as xylose rather than glycerol.

Figure 7:
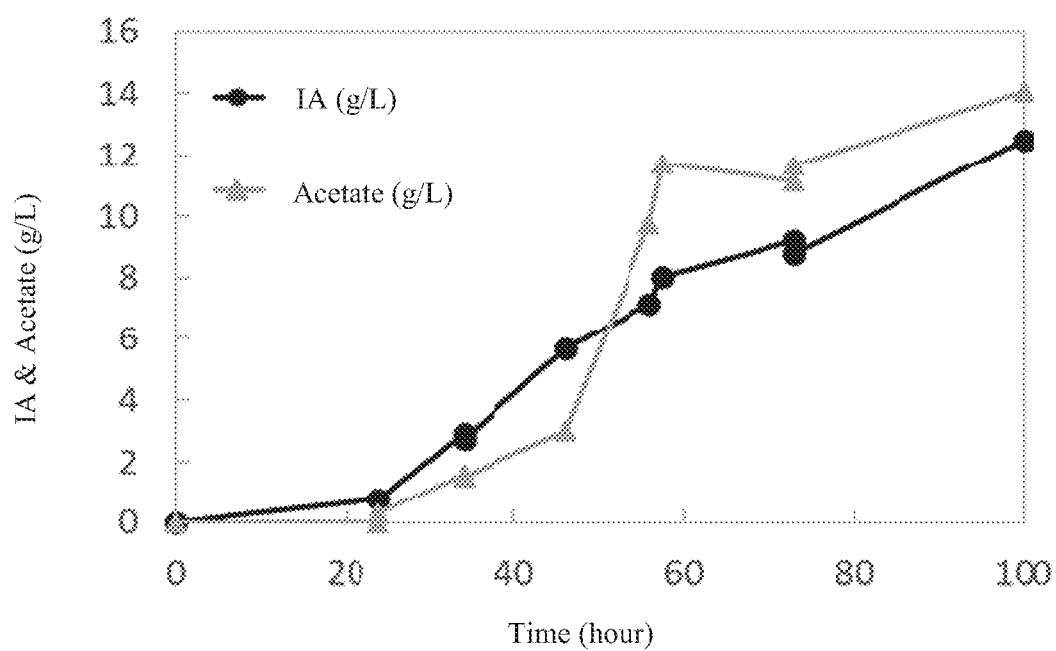
FIG. 7 is a data diagram of IA production titer and acetate titer at 30° C. and 30% dissolved oxygen.

Owing to the high oxygen requirement for efficient IA production, the dissolved oxygen level was thus increased to 30%. The result is shown in FIG. 7. FIG. 7 is a data diagram of IA production titer and acetate titer at 30° C. and 30% dissolved oxygen. As shown in FIG. 7, IA titer was successfully reached to 12.49 g/L in 100 hours via the increase of DO level. However, significant amount of acetate was detected to be 14 g/L in 100 hours as well. A great amount of acetate will induce pH and osmotic pressure to *E. coli*. For further optimizations of IA production, acetate formation is the major hurdle of the current fermentation process.

Example 5

Strategies for Directing Carbon Flux into IA Production

Figure 8:
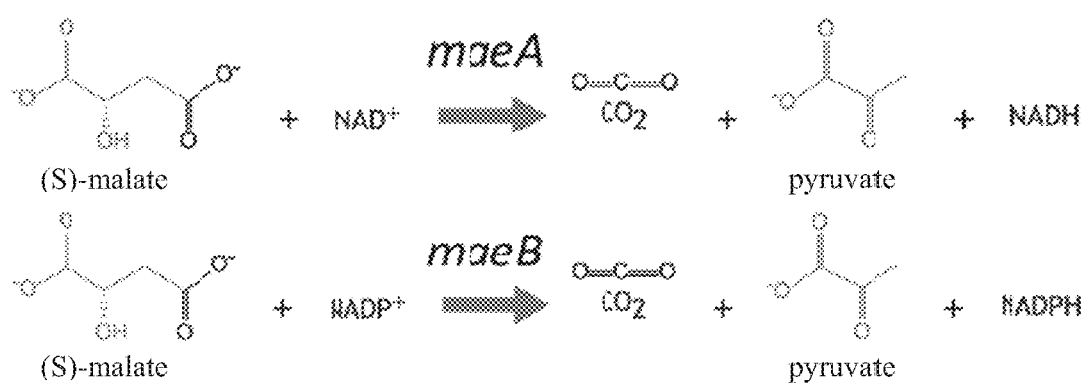
FIG. 8 is a schematic diagram showing gluconeogenesis from malate to pyruvate catalyzed by malate dehydrogenase (maeA and maeB both encode for malate dehydrogenase).

Observing from previous results, xylose was largely consumed rather than glycerol which implying the conversion of xylose into acetate. Xylose is assimilated to form α-KG α-KG then can take part in the subsequent reaction in the TCA cycle. When α-KG is converted into malate or oxaloacetate, there are several enzymes that can catalyze gluconeogenesis reaction to transform TCA cycle intermediates into central metabolites such as pyruvate and phosphoenolpyruvate. Hence, these xylose derived central metabolites can be further directed into acetate biosynthesis. Under the assumption of xylose overflow to form acetate via gluconeogenesis pathways, by blocking these pathways, the carbon flux from xylose can be suppressed so as to reduce acetate production. Researchers have reported the endogenous protein expression difference after icd was deleted in *E. coli*. Malate dehydrogenase (mae) was upregulated approximately 21-folds, which can prove the assumption of xylose overflow through the gluconeogenesis pathway. FIG. 8 is a schematic diagram showing gluconeogenesis from malate to pyruvate catalyzed by malate dehydrogenase (maeA and maeB both encode for malate dehydrogenase). As shown in FIG. 8, there are two malate dehydrogenases maeA and maeB in *E. coli*.

Figure 9:
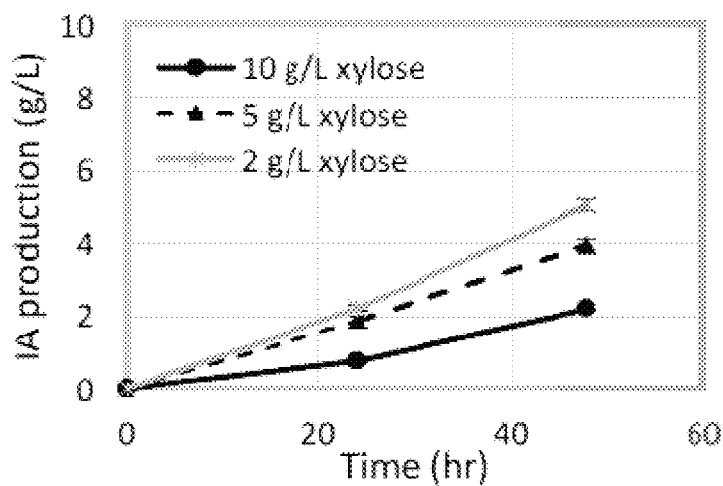
FIG. 9 is a data diagram showing the effect of different initial xylose concentrations on IA production.

In avoidance of TCA cycle intermediates accumulation, the nonphosphorylative pathway efficiency needs to be adjusted. Rather than placing adjustment on the aspect of gene modification, by lowering the initial xylose concentration in the culture medium, so that the pathway efficiency is adjusted to some extent. The result is shown in FIG. 9. FIG. 9 is a data diagram showing the effect of different initial xylose concentrations on IA production. As shown in FIG. 9, 2 g/L initial xylose concentration significantly enhances IA production compared with that of other initial xylose concentrations.

Example 6

*Escherichia coli* Transformant of Present Invention can Produce a Large Amount of IA in 1 L Bioreactor In this example, IA production was performed in the stirred-tank 1 L bioreactor (Major science). Single colonies were chosen from LB plates and inoculated into 2 mL of LB media contained in test tubes with the appropriate antibiotics (kanamycin 50 μg/mL and spectinomycin 50 μg/mL). The overnight culture grown in LB at 37° C. in a rotary shaker (250 rpm) was then inoculated (1%, v/v) into 25 mL LB at 37° C. for 24 hours. Centrifuging to separate LB and the cells, resuspended using filtered water to the same volume. 10% of the flask culture was then inoculated (10%, v/v) into 0.7 L bioreactor with M9 medium (12.8 g $Na_2HPO_4.7H_2O$, 3 g $KH_2PO_4$, 0.5 g NaCl, 1 g $NH_4Cl$, 1 mmol $MgSO_4$, 1 mg vitamin B1 and 0.1 mmol $CaCl_2$ per liter of water), 1000× trace metal mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 0.049 g $Co(NO_3)_2.6H_2O$ per liter water), 20 g/L glycerol with 5 g/L xylose, 0.1 mM IPTG and appropriate antibiotics. Dissolved oxygen (DO) was maintained at 20% or 30% with respect to air saturation by raising the stirrer speed (from 550 to 700 rpm). The aeration was set to 1 vvm (volume of gas per volume of liquid per minute). The pH was maintained at 7 by the automatic addition of 5 N NaOH. Xylose stock for feeding purpose is 300 g/L; glycerol is 600 g/L with 40 g/L ammonium sulfate.

Figure 10:
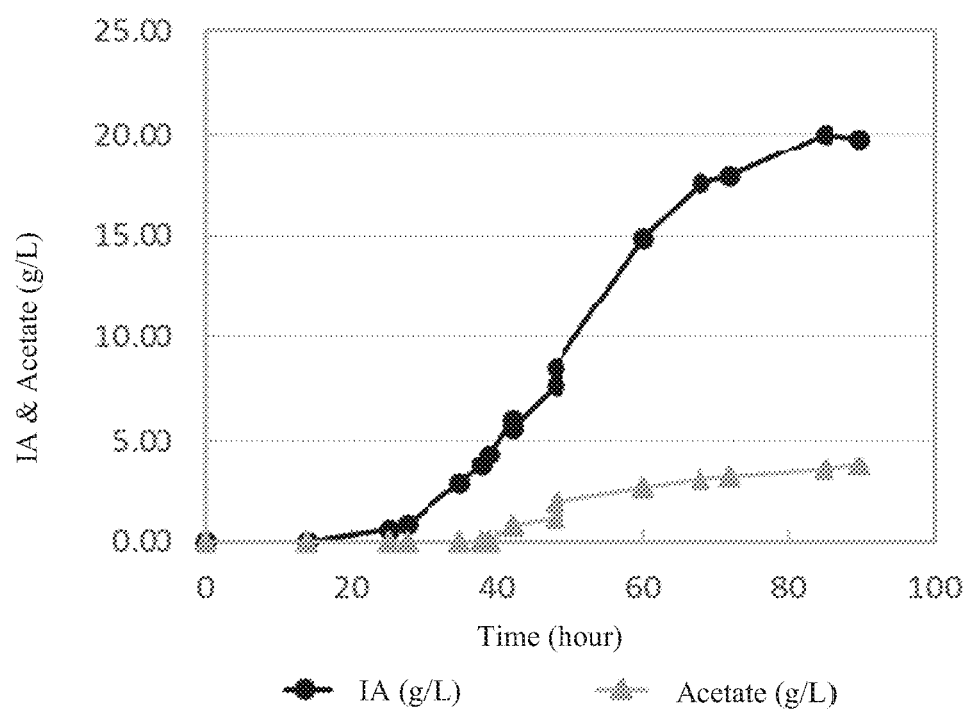
FIG. 10 is a data diagram showing the effect of the *Escherichia coli* transformant of the present invention on IA production scale up in the bioreactor.

Combining all the optimization process together, includes: one stage fermentation (keep at 30° C.) for better protein folding of Cad, control culture environment at high oxygen level (DO 30%), feed ammonium salts to prolong IA production and lower the initial xylose concentration. The result of this example is shown in FIG. 10. FIG. 10 is a data diagram showing the effect of the *Escherichia coli* transformant of the present invention (BW25113 ΔicdΔxylAΔyjhH ΔyagE+pKL7+pKL8) on IA production scale up in the bioreactor. As shown in FIG. 10, integrating all this optimization condition, the *Escherichia coli* transformant of the present invention successfully produces 20.01 g/L IA in 90 hours with yield 0.62 (g IA/g glycerol) and productivity 0.24 g/L/hr. Most importantly, high yield (86% of theoretical yield) of IA production with little amount of acetate as byproduct (3.7 g/L).

Comparative Example

Effect of ΔmaeA ΔmaeB Double Knockout Strain on IA Production and Acetate Accumulation The maeA and maeB double knockout strain (BW25113 Δicd ΔxylA ΔyjhH ΔyagE ΔmaeA ΔmaeB) was then constructed for IA production test. The result is shown in FIG. 11.

Figure 11:
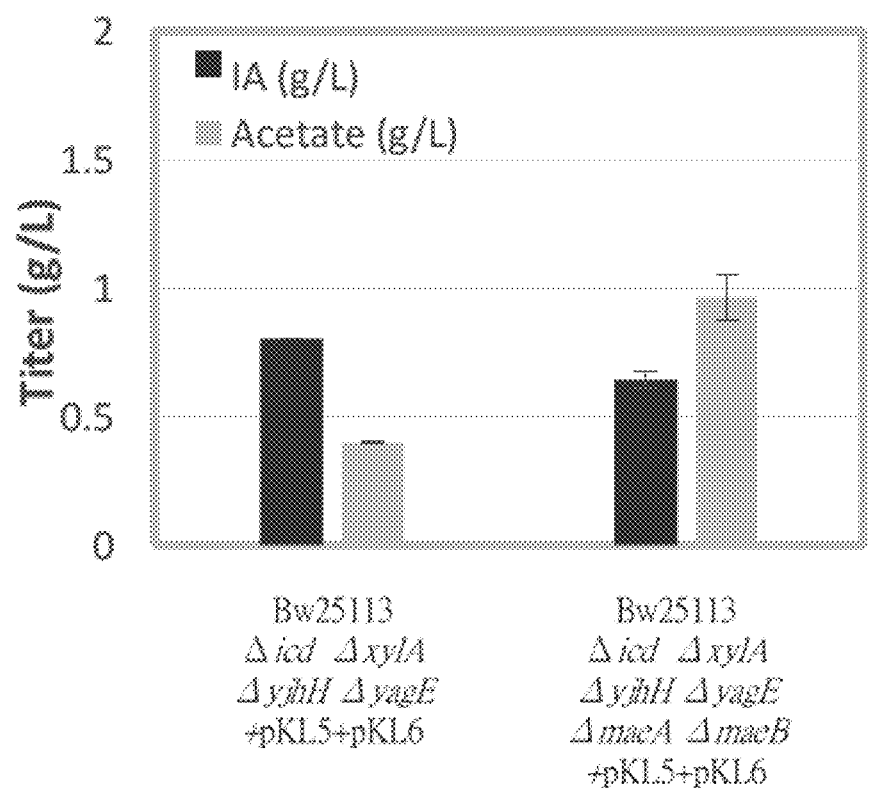
FIG. 11 is a data diagram showing the effect of the ΔmaeA ΔmaeB double knockout strain of the present invention on affecting IA production and acetate accumulation, in which BW25113 Δicd ΔxylA ΔyjhH ΔyagE+pKL5+pKL6 indicates the *Escherichia coli* strain in which maeA and maeB genes are not deleted; BW25113 Δicd ΔxylA ΔyjhH ΔyagE ΔmaeA ΔmaeB+pKL5+pKL6 indicates the *Escherichia coli* strain in which maeA and maeB genes are deleted.

FIG. 11 is a data diagram showing the effect of the ΔmaeA ΔmaeB double knockout strain of the present invention on affecting IA production and acetate accumulation. As shown in FIG. 11, inactivation of these two genes resulted in acetate increase and IA titer reduction. The result may attribute to the accumulation of TCA cycle intermediates thus hinder the entering carbon flux from central metabolites such as acetyl-CoA which can be easily directed into acetate.

In summary, the *Escherichia coli* transformant of the present invention certainly has the effect of: by constructing a heterologous metabolic pathway, the nonphosphorylative pathway of *Burkholderia xenovorans* in *Escherichia coli*, enables the strain to self-convert to synthesize α-ketoglutaric acid and further synthesize glutamate by metabolizing xylose. Furthermore, in the medium without additional protein nutrient source, the growth of the *Escherichia coli* transformant of the present invention is optimized that the original cell concentration of $OD_{600}$ is 0.296 (36 hours) (before optimization of gene combination), and the optimized cell concentration of $OD_{600}$ is 1.62 (36 hours)(after optimization of gene combination) through the optimization of gene combination. Using glycerol and xylose can increase IA production and optimize cell growth, and the yield of IA can reach 1.2 g/L (24 hours) by eliminating the competitive pathways of the nonphosphorylative metabolic pathway. The experimental results of the present invention confirm that reducing the initial concentration of xylose in the medium can increase the yield of IA by 2.2 g/L (24 hours), and in combination with the above optimized conditions, the process is amplified in a 1 liter fermentation tank (i.e., a bioreactor), the yield of IA can achieve 20.01 g/L (90 hours), 0.62 (g IA/g glycerol), and 0.24 g/L/hour productivity in minimal medium. The IA titer can reach 1.4 g/L in 24 hours (cultured in the flask in minimal medium without additional protein nutrient source).

Although the present invention has been described with reference to the preferred embodiments, it will be apparent to those skilled in the art that a variety of modifications and changes in form and detail may be made without departing from the scope of the present invention defined by the appended claims.

What is claimed is:

1. An *Escherichia coli* transformant, comprising at least one plasmid, wherein the at least one plasmid includes a D-xylose dehydrogenase (XDH) gene, a D-xylonolactonase (XL) gene, a 2-keto-3-deoxy-D-xylonate dehydratase (KdxD) gene, and a 2-ketoglutarate semialdehyde dehydrogenase (KGSADH) gene;
   wherein an isocitrate dehydrogenase (icd) gene of the *Escherichia coli* transformant is deleted;
   wherein the at least one plasmid further includes a D-xylonate dehydratase (XD) gene;
   wherein the XDH gene, the XL gene, the KdxD gene, the KGSADH gene, and the XD gene are obtained from *Burkholderia xenovorans* strains;
   wherein the XDH gene, the XL gene, the XD gene, the KdxD gene, and the KGSADH gene are sequentially constructed from their 5' ends to 3' ends in the at least one plasmid;
   wherein the *Escherichia coli* transformant is a transformant of *Escherichia coli* BW25113;
   wherein the *Escherichia coli* transformant converts xylose into α-ketoglutaric acid through a nonphosphorylative metabolic pathway;
   wherein a xylose isomerase gene (xylA), a 2-dehydro-3-deoxy-D-pentonate aldolase gene (yjhH), and a 2-keto-3-deoxygluconate aldolase gene (yagE) of the *Escherichia coli* transformant are deleted;
   wherein the *Escherichia coli* transformant produces itaconate without adding a yeast extract or glutamate; and
   wherein the at least one plasmid is pKL7 and pKL8.

2. The *Escherichia coli* transformant according to claim 1, further comprising a citrate synthase (gltA), an aconitase B (acn B), and a pyruvate carboxylase (pyc).

* * * * *